United States Patent [19]

Springer et al.

[11] Patent Number: 5,021,559
[45] Date of Patent: Jun. 4, 1991

[54] WATER-SOLUBLE AZO COMPOUNDS CONTAINING A FIBER-REACTIVE GROUP OF THE VINYLSULFONE SERIES, SUITABLE AS DYESTUFFS

[75] Inventors: Hartmut Springer, Königstein/Taunus; Uwe Reiher, Frankfurt am Main, both of Fed. Rep. of Germany

[73] Assignee: Hoechst Aktiengesellschaft, Frankfurt am Main, Fed. Rep. of Germany

[21] Appl. No.: 526,176

[22] Filed: May 21, 1990

[30] Foreign Application Priority Data

May 23, 1989 [DE] Fed. Rep. of Germany ....... 3916712

[51] Int. Cl.$^5$ .................. C09B 62/85; C09B 62/51; C09B 62/513; D06P 1/382; D06P 1/384
[52] U.S. Cl. .................. 534/638; 534/582; 534/617; 534/642; 534/887; 562/868; 564/163; 564/440
[58] Field of Search ......................... 534/638, 642

[56] References Cited

U.S. PATENT DOCUMENTS 3,184,280  5/1965  Zerweck et al. ............ 534/642 X
4,818,814  4/1989  Schlafer .................... 534/642

FOREIGN PATENT DOCUMENTS 1386165  3/1975  United Kingdom ............ 534/642

OTHER PUBLICATIONS

*Chemical Abstracts,* vol. 104, No. 52061f, (1985).

*Primary Examiner*—Mary C. Lee
*Assistant Examiner*—Fiona T. Powers

[57] ABSTRACT

Water-soluble azo compounds of the general formula D—N=N—K are described, which have advantageous fiber-reactive dye properties and dye carboxamido-containing and in particular hydroxy-containing materials, such as wool and in particular cellulose fiber materials, in hues which have high color strength and good fastness properties.

In the formula D—N=N—K, the symbols have the following meanings:

D is a radical of the general formula

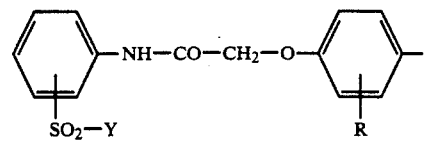

in which Y is a vinyl group or an ethyl group which can be eliminated in the $\beta$-position by an alkaline radical and R is a hydrogen atom, a nitro, lower alkyl, lower alkoxy, carboxyl or hydroxyl group or a halogen atom;

K is a radical of a mono-coupleable water-soluble coupling component, which can additionally contain an azo group, or the radical of a doubly-coupleable water-soluble coupling component, each from the series of aminobenzenes, phenols, naphthols, aminonaphthols, acylaminonaphthols, dihydroxynaphthalenesulfonic acids, phenylazoaminonaphtholsulfonic acids, naphthylazoaminonaphtholsulfonic acids, 5-pyrazolones, 5-aminopyrazoles, acetoacetylarylides, 2-hydroxy-6-pyridones and hydroxyquinolines, it also being possible for K to contain, in addition to the substituents customary in dyes, one or more fiber-reactive groups. Furthermore, precursors of these azo compounds of the general formula

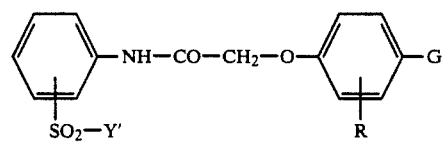

are described, in which G is an amino or nitro group, R has the abovementioned meaning and Y' is a $\beta$-hydroxyethyl group or has one of the meanings given above for Y.

14 Claims, No Drawings

WATER-SOLUBLE AZO COMPOUNDS CONTAINING A FIBER-REACTIVE GROUP OF THE VINYLSULFONE SERIES, SUITABLE AS DYESTUFFS

The present invention is in the technical field of fiber-reactive dyes.

New water-soluble azo compounds of the general formula (1)

D—N=N—K          (1)

having valuable fiber-reactive dye properties have now been found.

In this formula (1),

D is a radical of the general formula (2)

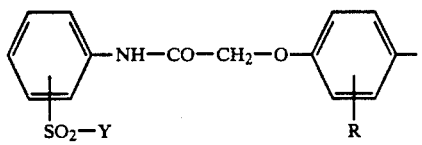

in which

Y is a vinyl group or a group of the general formula (3)

—CH$_2$—CH$_2$—X          (3)

in which

X is a substituent which can be eliminated by alkali with the formation of a vinyl group, the group —SO$_2$—Y being preferably bound to the benzene ring in the meta- or para-position with respect to the amidocarbonyl group, and R is a hydrogen atom, a nitro group, an alkyl group of 1 to 4 carbon atoms, such as an ethyl and in particular a methyl group, an alkoxy group of 1 to 4 carbon atoms, such as an ethoxy and in particular a methoxy group, a carboxy group, a hydroxy group or a halogen atom, such as a chlorine or a bromine atom, but is preferably a hydrogen atom;

K is a radical of a mono-coupleable water-soluble coupling component, which can additionally contain an azo group, or the radical of a doubly-coupleable water-soluble coupling component, each from the series of aminobenzenes, phenols, in particular their sulfonic acids and carboxylic acids, naphthols, in particular their sulfonic acids and carboxylic acids, aminonaphthols, in particular their sulfonic acids, acylaminonaphthols, in particular their sulfonic acids, with the acyl radical of an alkane- or alkenecarboxylic acid each having 1 to 4 or 2 to 4 carbon atoms in the alkyl or alkenyl radical or of an aromatic carboxylic acid, such as benzoic acid, or of an aromatic sulfonic acid, such as benzene- or toluenesulfonic acid, or of an N-substituted carbamic acid, such as the N-phenylureido radical, or from the series of dihydroxynaphthalenesulfonic acids, phenylazo- and naphthylazoaminonaphtholsulfonic acids, 5-pyrazolones and 5-aminopyrazoles, acetoacetylarylides, 2-hydroxy-6-pyridones and hydroxyquinolines, it also being possible for K to contain one or more fiber-reactive groups in addition to the substituents customary in dyes, such as, for example, a group —SO$_2$—Y where Y has the abovementioned meaning or a 4-fluoro- or 4-chloro-6-amino-s-triazin-2-ylamino group whose amino group in the 6-position can be mono- or disubstituted by alkyl of 1 to 4 carbon atoms and/or phenyl, it being possible for the phenyl radical to be substituted by substituents from the group comprising sulfo, carboxy, methoxy, ethoxy, methyl, chlorine, bromine and —SO$_2$—Y where Y has the above-mentioned meaning.

Alkali-eliminatable substituents X are, for example, halogen atoms, such as a bromine atom and a chlorine atom, ester groups of organic carboxylic and sulfonic acids, such as an alkanoyloxy radical of 2 to 5 carbon atoms, for example an acetoxy group, or a sulfobenzoyloxy, benzoyloxy, phenylsulfonyloxy or toluenesulfonyloxy radical, furthermore, for example, phosphato, sulfato and thiosulfato groups, as well as dialkylamino groups containing alkyl groups of 1 to 4 carbon atoms each, such as a dimethylamino and diethylamino group.

Y is preferably a vinyl group and in particular a $\beta$-sulfatoethyl group.

Sulfo groups are groups of the general formula —SO$_3$M, carboxy groups are groups of the general formula —COOM, sulfato groups are groups of the general formula —OSO$_3$M, thiosulfato groups are groups of the general formula —S—SO$_3$M and phosphato groups are groups of the general formula —O-PO$_3$M$_2$, in which M is a hydrogen atom or a salt-forming metal atom, such as, in particular, an alkali metal atom, such as, for example, sodium, potassium or lithium.

Of the compounds according to the invention of the general formula (1), for example, those compounds may be mentioned in particular in which K is a radical of the formula (4a), (4b), (4c), (4d), (4e), (4f), (4g), (4h), (4i), (4k), (4m), (4n), (4p), (4q), (4r), (4s), (4t), (4v) and (4w) below:

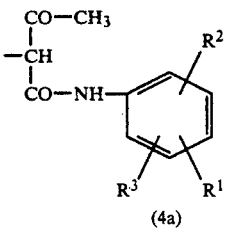

(4a)

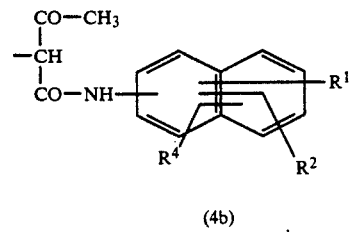

(4b)

-continued
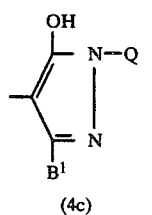
(4c)
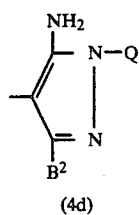
(4d)
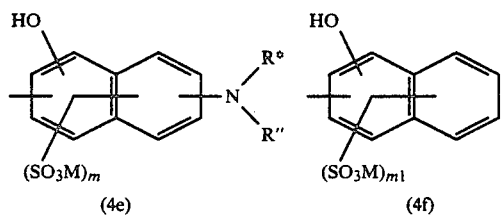
(4e)   (4f)
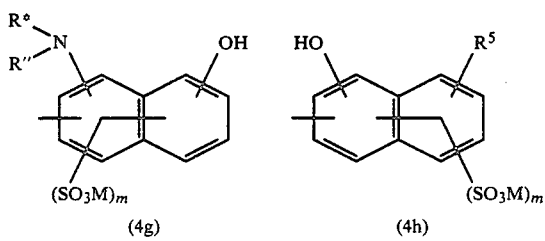
(4g)   (4h)
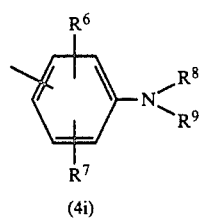
(4i)
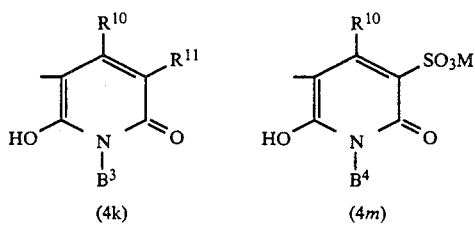
(4k)   (4m)
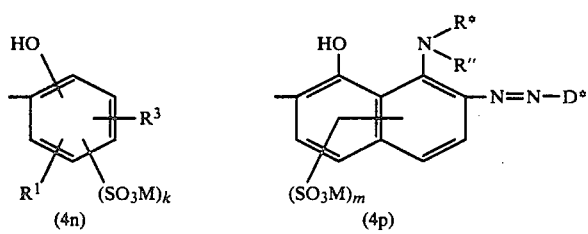
(4n)   (4p)
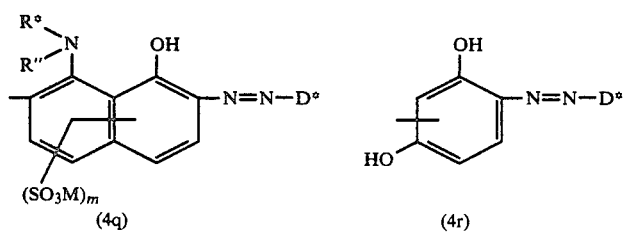
(4q)   (4r)

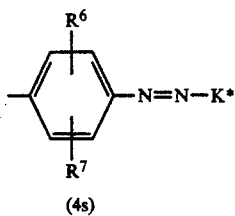 (4s)

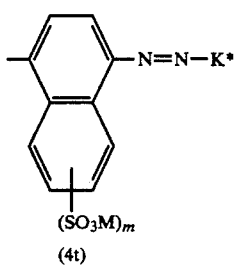 (4t)

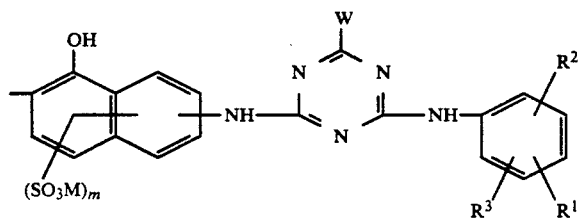 (4v)

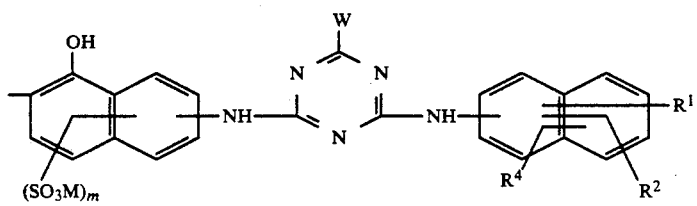 (4w)

In these formulae, the symbols have the following meanings:

$R^1$ is hydrogen, carboxy, sulfo or a group of the general formula —SO$_2$—Y where Y has the above meaning;

$R^2$ is hydrogen, alkyl of 1 to 4 carbon atoms, such as methyl and ethyl, alkoxy of 1 to 4 carbon atoms, such as methoxy and ethoxy, chlorine, bromine, carboxy, sulfo or nitro;

$R^3$ is hydrogen, alkyl of 1 to 4 carbon atoms, such as methyl and ethyl, alkoxy of 1 to 4 carbon atoms, such as methoxy and ethoxy, chlorine or bromine;

$R^4$ is hydrogen, sulfo or carboxy, preferably hydrogen, if $R^1$ is a group —SO$_2$—Y;

$B^1$ is alkyl of 1 to 4 carbon atoms, such as methyl, carboxy, carbalkoxy of 2 to 5 carbon atoms, such as carbomethoxy and carbethoxy, carbamoyl, phenyl or phenyl substituted by sulfo, carboxy, methyl, ethyl, methoxy, ethoxy and/or chlorine;

$B^2$ is alkyl of 1 to 4 carbon atoms, such as methyl, carboxy, carbalkoxy of 2 to 5 carbon atoms, such as carbomethoxy and carbethoxy, carbamoyl, phenyl or phenyl substituted by 1 or 2 substituents from the group comprising alkyl of 1 to 4 carbon atoms, alkoxy of 1 to 4 carbon atoms, chlorine, bromine and sulfo;

Q is phenyl, which can be substituted, such as, for example, by 1, 2 or 3, preferably 1 or 2, substituents from the group comprising chlorine, bromine, methyl, ethyl, methoxy, ethoxy, carboxy, sulfo and alkanoylamino of 2 to 5 carbon atoms, such as acetylamino, and/or by a group of the general formula —SO$_2$—Y where Y has the abovementioned meaning, or is naphthyl, which can be substituted by 1, 2 or 3 sulfo and, if desired, 1 alkyl of 1 to 4 carbon atoms, 1 alkoxy of 1 to 4 carbon atoms, 1 chlorine or 1 alkanoylamino of 2 to 5 carbon atoms and/or by a group of the general formula —SO$_2$—Y where Y has the abovementioned meaning;

R* is hydrogen or alkyl of 1 to 4 carbon atoms, which can be substituted by phenyl or by phenyl which is substituted by sulfo and/or —SO$_2$—Y where Y has the above meaning;

R" is hydrogen or alkyl of 1 to 4 carbon atoms, which can be substituted by phenyl, sulfophenyl or a group of the formula —SO$_2$—Y where Y has the above meaning, or is phenyl or phenyl substituted by 1 or 2 substituents from the group comprising alkyl of 1 to 4 carbon atoms, alkoxy of 1 to 4 carbon atoms, chlorine, bromine, sulfo and —SO$_2$—Y where Y has the above meaning;

$R^5$ is phenylureido, the phenyl radical of which can be substituted by a group of the formula —SO$_2$—Y where Y has the above meaning, or is alkanoylamino of 2 to 5 carbon atoms, such as acetylamino or propionylamino, which can be substituted in the alkyl radical by a group of the formula —SO$_2$—Y where Y has the above meaning, or is alkenoylamino of 3 to 5 carbon atoms, such as acryloylamino, or is benzoylamino, which can be substituted by substituents from the group comprising chlorine, methyl, methoxy, nitro, sulfo, carboxy and —SO$_2$—Y where Y has the above meaning, and is preferably acetylamino or benzoylamino;

$R^6$ is hydrogen, alkyl of 1 to 4 carbon atoms, alkoxy of 1 to 4 carbon atoms, sulfo, carboxy, carbalkoxy of 2 to 5 carbon atoms, such as carbomethoxy and carbethoxy, halogen, such as bromine or chlorine, or alkoxy of 1 to 4 carbon atoms which is substituted by hydroxy, acetyloxy, carboxy, carbamoyl, cyano or halogen, such as chlorine;

$R^7$ is hydrogen, alkyl of 1 to 4 carbon atoms, alkoxy of 1 to 4 carbon atoms, halogen, such as bromine or chlorine, cyano, trifluoromethyl, alkoxy of 1 to 4 carbon atoms which is substituted by hydroxy, acetyloxy, carboxy, carbamoyl or cyano or halogen, such as chlorine, or by a group of the formula —SO$_2$—Y where Y has the above meaning, or is alkanoylamino of 2 to 5 carbon atoms, which can be substituted by chlorine, bromine, alkoxy of 1 to 4 carbon atoms, phenoxy, phenyl, hydroxy, carboxy or sulfo or a group of the formula —SO$_2$—Y where Y has the above meaning, or is alkenoylamino of 3 to 5 carbon atoms, which can be substituted by chlorine, bromine, carboxy or sulfo, or is benzoylamino, which can be substituted in the benzene ring, for example by substituents from the group comprising chlorine, methyl, sulfo and a group of the formula —SO$_2$—Y where Y has the above meaning, or is alkylsulfonyl of 1 to 4 carbon atoms or phenylsulfonyl, which can be substituted in the benzene ring, for example by substituents from the group comprising chlorine, methyl, sulfo and a group of the formula —SO$_2$—Y where Y has the above meaning, or is alkylsulfonylamino of 1 to 4 carbon atoms, which can be substituted by hydroxy, sulfato, chlorine, bromine, alkoxy of 1 to 4 carbon atoms or a group of the formula —SO$_2$—Y where Y has the above meaning, or is phenylsulfonylamino, which can be substituted in the benzene ring, for example by substituents from the group comprising chlorine, methyl, sulfo and a group of the formula —SO$_2$—Y where Y has the above meaning, or is carbamoyl, which can be monosubstituted or disubstituted on the nitrogen atom by one or two substituents which belong to the group comprising alkyl of 1 to 4 carbon atoms, alkyl of 1 to 4 carbon atoms which is substituted, for example, by hydroxy, sulfo, carboxy, sulfato or phenyl or a group of the formula —SO$_2$—Y where Y has the above meaning, cycloalkyl of 5 to 8 carbon atoms, phenyl and phenyl which is substituted by substituents, for example, from the group comprising chlorine, sulfo, methyl, methoxy, carboxy and a group of the formula —SO$_2$—Y where Y has the above meaning, or is sulfamoyl, which can be mono- or disubstituted on the nitrogen atom by 1 or 2 substituents which belong to the group comprising alkyl of 1 to 4 carbon atoms, alkyl of 1 to 4 carbon atoms which is substituted by substituents, for example, from the group comprising hydroxy, sulfo, carboxy, sulfato or phenyl or a group of the formula —SO$_2$—Y where Y has the above meaning, cycloalkyl of 5 to 8 carbon atoms, phenyl and phenyl which is substituted by substituents, for example, from the group comprising chlorine, sulfo, methyl, methoxy, carboxy and a group of the formula —SO$_2$—Y where Y has the above meaning, or is ureido or ureido which can be mono- or disubstituted on the terminal nitrogen atom by 1 or 2 substituents which belong to the group comprising alkyl of 1 to 4 carbon atoms, alkyl of 1 to 4 carbon atoms which is substituted, for example, by hydroxy, sulfo, carboxy, sulfato, phenyl or a group of the formula —SO$_2$—Y where Y has the above meaning, cycloalkyl of 5 to 8 carbon atoms, phenyl and phenyl which is substituted by substituents, for example, from the group comprising chlorine, sulfo, methyl, methoxy, carboxy and a group of the formula —SO$_2$—Y where Y has the above meaning;

$R^8$ is hydrogen or alkyl of 1 to 4 carbon atoms, which can be substituted, for example, by hydroxy, sulfo, carboxy, sulfato, a group —SO$_2$—Y where Y has the above meaning, phenyl or sulfophenyl, or is alkenyl of 2 to 4 carbon atoms, which can be substituted by carboxy, sulfo, chlorine or bromine, or is cycloalkyl of 5 to 8 carbon atoms;

$R^9$ is hydrogen or alkyl of 1 to 4 carbon atoms, which can be substituted, for example, by hydroxy, sulfo, carboxy, sulfato, phenyl or —SO$_2$—Y where Y has the above meaning, or is alkenyl of 2 to 5 carbon atoms, which can be substituted by carboxy, sulfo or —SO$_2$—Y where Y has the above meaning or by chlorine or bromine, or $R^9$ is cycloalkyl of 5 to 8 carbon atoms or phenyl, which can be substituted, for example, by substituents from the group comprising chlorine, sulfo, methyl, methoxy, carboxy and —SO$_2$—Y where Y has the above meaning, or $R^8$ and $R^9$ together with the nitrogen atom and optionally with a further heteroatom or hetero group, such as N, O, S or NH, represent a 5- to 8-membered, preferably saturated, heterocyclic radical, such as, for example, an N-piperidino, N-morpholino or N-piperazino radical;

$R^{10}$ is hydrogen or alkyl of 1 to 4 carbon atoms or alkyl of 1 to 4 carbon atoms which is substituted by alkoxy of 1 to 4 carbon atoms or cyano;

$R^{11}$ is hydrogen, sulfo, sulfoalkyl having an alkyl radical of 1 to 4 carbon atoms, such as sulfomethyl, cyano or carbamoyl;

$B^3$ is hydrogen or alkyl of 1 to 6 carbon atoms, preferably of 1 to 4 carbon atoms, which can be substituted by phenyl, sulfo, sulfophenyl or —SO$_2$—Y where Y has the above meaning;

$B^4$ is hydrogen, alkyl of 1 to 4 carbon atoms or alkyl of 1 to 4 carbon atoms which is substituted by alkoxy of 1 to 4 carbon atoms, such as methoxy, sulfo, carboxy, sulfato, acetylamino, benzoylamino or cyano or by a group of the formula —SO$_2$—Y where Y has the above meaning, or is alkenyl of 2 to 4 carbon atoms, cyclohexyl, phenyl or phenyl which is substituted by substituents from the group comprising carboxy, sulfo, benzoylamino, acetylamino, —SO$_2$—Y where Y has the above meaning and chlorine;

k is the number zero or 1 (where, in the case that k is zero, this group is a hydrogen atom);

m is the number 1 or 2;

m is the number 1, 2 or 3;

D* is a group of the general formula (2) or is phenyl, which can be substituted by 1, 2 or 3, preferably 1 or 2, substituents from the group comprising alkyl of 1 to 4 carbon atoms, alkoxy of 1 to 4 carbon atoms, chlorine, bromine, hydroxy, carboxy, sulfo, carbamoyl, sulfamoyl and alkanoylamino of 2 to 5 carbon atoms, of these, preferably methyl, methoxy, ethoxy, chlorine, sulfo, carboxy and hydroxy, and/or by a group of the formula —SO$_2$—Y where Y has the above meaning, one of these substituents being preferably a sulfo or carboxy group and the group —SO$_2$—Y being preferably in the meta- or para-position relative to the azo group, or D* is naphthyl which is substituted by 1, 2 or 3 sulfo groups or by 1 or 2 sulfo groups and 1 or 2 groups of the general formula —SO$_2$—Y where Y has the abovementioned meaning or only by one of these groups —SO$_2$—Y, it being possible for D and D* to have meanings which are identical to or different from one another;

K* is a radical of one of the general formulae (4a) to (4m) mentioned and defined above, it being possible for K and K* to have meanings which are identical to or different from one another;

W is sulfo, alkylsulfonyl of 1 to 4 carbon atoms, phenylsulfonyl or bromine or preferably fluorine or chlorine;

M has one of the abovementioned meanings.

The individual formula members, including the formula members which may occur twice in the same formula, can have meanings which are identical to or different from one another.

The free bonds present in the above formulae (4e), (4f), (4g), (4h), (4i) and (4n) and leading to the azo group, and the azo group in formula (4p) and (4q) are bound in the ortho-position relative to the hydroxy or amino group. This hydroxy group is preferably bound to the naphthalene radical in the α-position.

Alkyl groups of 1 to 4 carbon atoms are preferably the ethyl and in particular the methyl group; alkoxy groups of 1 to 4 carbon atoms are preferably the ethoxy and in particular the methoxy group; alkanoylamino groups of 2 to 5 carbon atoms are preferably the propionylamino group and in particular the acetylamino group, and carbalkoxy groups of 2 to 5 carbon atoms are preferably the carbomethoxy and carbethoxy groups.

Of the compounds according to the invention of the general formula (1), in particular those are preferred in which K is a radical of the general formula (4c), (4f), (4h), (4p) or (4q), in which in turn the individual formula members have the following preferred meanings:

$B^1$ is carboxy or methyl;

Q is phenyl, which can be substituted by 1 or 2 substituents which are selected from the following group of substituents: 2 methyl, 2 methoxy, 1 chlorine or bromine, 2 sulfo, 1 carboxy and 1 vinylsulfonyl or β-sulfatoethylsulfonyl;

$R^5$ is acetylamino, propionylamino, or benzoylamino which can be substituted by 1 or 2 substituents from the group comprising chlorine, methyl, methoxy, nitro, sulfo and β-sulfatoethylsulfonyl;

R* and R" are both hydrogen;

m in formula (4p) and (4q) is the number 2, and the one group —$SO_3M$ is in the meta position relative to the hydroxy group and the other group —$SO_3M$ in the meta or para position to the amino group.

Particular preference is given to those compounds of the general formula (1) in which K is a 1-hydroxy-2-naphthyl radical which is substituted by 1, 2 or 3 sulfo groups or a radical of the general formula (4c) in which $B^1$ is a carboxy or methyl group and Q is a phenyl radical which is substituted by 1 or 2 substituents selected from the group comprising 2 methyl groups, 2 ethoxy groups, 2 methoxy groups, 2 sulfo groups, 1 carboxy group or 1 chlorine atom, in which one of the substituents must be a carboxy or sulfo group, or the phenyl radical is substituted by a vinylsulfonyl or β-sulfatoethylsulfonyl group and can additionally be substituted by 1 or 2 substituents selected from the group comprising 1 methyl, 2 methoxy, 1 chlorine and 1 sulfo.

$R^1$ in the component K of the general formula (4v) is preferably a group —$SO_2$—Y where Y has the abovementioned, in particular preferred, meaning, $R^2$ is a hydrogen atom, an alkyl group of 1 to 4 carbon atoms, an alkoxy group of 1 to 4 carbon atoms, a chlorine or bromine atom or a carboxy, sulfo or nitro group and $R_3$ is a hydrogen atom.

The present invention furthermore relates to processes for the preparation of the azo compounds according to the invention of the general formula (1), for example by coupling reaction of the diazonium compound of an amino compound of the general formula (5)

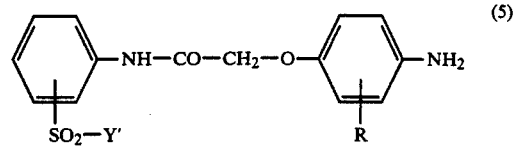

in which Y' has one of the meanings of Y or is the β-hydroxyethyl group and R has the abovementioned meaning, with a coupling component of the general formula H-K where K has the abovementioned meaning; if K, as mentioned above, is a divalent coupling component, a disazo compound if desired can be prepared by reaction of this divalent coupling component with a two-fold equimolar amount of the diazo component. In the case where a compound (5) in which Y' is a β-hydroxyethyl group is used, this β-hydroxyethyl group in the resulting azo compound is converted into a group Y of the azo compound according to the invention (1), as will be described later.

The diazotization and coupling reactions are carried out in the usual and long-known manner, for example the diazotization of the amine (5), as a rule, at a temperature between −5° C. and +15° C. and a pH below 2 by means of a strong acid and alkali metal nitrite in, preferably, aqueous medium, and the coupling reaction, as a rule, at a pH between 1.5 and 4.5 in the case of an amino-containing coupling component and at a pH between 3 and 7.5 in the case of a hydroxy-containing coupling component and at a temperature between 0° and 30° C. in, preferably, aqueous medium. If the coupling component is a divalent, di-coupleable compound, it contains, for example, a coupleable amino group and, at the same time, a coupleable hydroxy group, a disazo compound can be prepared by carrying out the coupling reaction first with the first mole of the diazonium compound of the amine in the acidic pH range to form the monoazo compound and the second coupling reaction with the second mole of the diazonium compound of the amine subsequently in the weakly acidic to weakly alkaline range. This procedure applies, for example, to the compounds of the general formulae (4p) and (4q), for example by coupling the aminonaphtholsulfonic acid first with the first mole of the diazonium compound of the amine of the general formula (5) or any other aromatic amine of the general formula D*—$NH_2$ where D* has the abovementioned meaning different from D in acidic medium and then by coupling the resulting monoazo compound with the second mole of a diazonium compound of an amine D*—$NH_2$ where D* has the abovementioned meaning, in the weakly acidic, neutral or weakly alkaline range, it being necessary for D* to have one of the meanings given for D, if the first coupling reaction was not carried out using a diazonium compound of an amine (5), for example, in particular, first at a pH of about 1 to 2.5 and then at a pH between 4 and 6.5, in which, if the diazonium compound of the amino compound (5) in both coupling reactions is identical, it is possible to carry out the first and second coupling reaction in one and the same batch, first in the acidic range mentioned and then in the weakly acidic to weakly alkaline range. To prepare a disazo compound of the general formula (4r), the reaction of the coupling component resorcinol with the diazonium compound(s) is advantageously first carried out at a pH of between 0.8 and 2 and then at a pH between 6 and 7.5.

Disazo compounds of the general formula (1) whose radical K corresponds to the radical of an azo compound composed of a coupleable diazo component and a coupling component, such as, for example, a radical of the general formula (4s) or (4t), can also be prepared according to the invention by first coupling the diazonium compound of an amine (5) with the amino-containing and thus diazotizable coupling component, such as, for example, in formulae (4s) and (4t), the aniline and sulfo-aminonaphthalene components substituted by the substituents $R^6$ and $R^7$, and diazotizing the amino group in the aminoazo compound thus formed and coupling it with a coupling component, such as, for example, the coupling component H—K*, to give the disazo compound.

All these possible reactions for synthesizing disazo compounds are analogous to the methods known in the literature or known to one skilled in the art for the synthesis of disazo compounds.

Examples of coupling components which can be used for the preparation of the dyes according to the invention and have, for example, the general formulae (4a) to (4n) are: 1,3-diamino-benzene-5-sulfonic acid, phenol, cresol, resorcinol, 2-ethoxyphenol, 4-methylphenol, 3-sulfophenol, salicylic acid, 3-sulfo-1-naphthol, 4-sulfo-1-naphthol, 5-sulfo-1-naphthol, 3,6-disulfo-8-naphthol, 4,6-disulfo-8-naphthol, 1-naphthol-3,8-disulfonic acid, 1-amino-8-naphthol-4-sulfonic acid, 1-amino-8-naphthol-5-sulfonic acid, 1-amino-8-naphthol-2,4-disulfonic acid, 2-amino-5-naphthol-7-sulfonic acid, 2-amino-5-naphthol-1,7-disulfonic acid, 1-amino-5-naphthol-7-sulfonic acid, 2-amino-8-naphthol-6-sulfonic acid, 2-amino-8-naphthol-3,6-disulfonic acid, 2-amino-8-naphthol-4,6-disulfonic acid, 1-amino-8-naphthol-3,6- or -4,6-disulfonic acid, 1-acryloylamino-8-naphthol-3,6- or -4,6-disulfonic acid, 1-propionylamino-8-naphthol-3,6- or -4,6-disulfonic acid, 1-acetylamino-8-naphthol-4-sulfonic acid, 1-acetylamino-8-naphthol-3,6- or -4,6-disulfonic acid, 1-benzoylamino-8-naphthol-3,6- or -4,6-disulfonic acid, 2-naphthol-5,7-disulfonic acid, 2-naphthol-3,6- and -6,8-disulfonic acid, 1,8-dihydroxynaphthalene-3,6-disulfonic acid, 1,8-dihydroxynaphthalene-6-sulfonic acid, 1-naphthol-3,6,8-trisulfonic acid, 2-acetylamino-5-naphthol-7-sulfonic acid, 2-benzoylamino-8-naphthol-6-sulfonic acid, 2-(p'-tosylamino)-5-naphthol-7-sulfonic acid, 2-acetylamino-8-naphthol-3,6-disulfonic acid, 2-acetylamino-5-naphthol-1,7-disulfonic acid, 3-benzoylamino-8-naphthol-6-sulfonic acid, 2-phenylsulfonylamino-5-naphthol-7-sulfonic acid, 2-(N-methyl-N-acetyl)amino-8-naphthol-6-sulfonic acid, N-ethyl-N-benzylaniline-3-sulfonic acid, N,N-bis-($\beta$-hydroxyethyl)aniline, N,N-bis-($\beta$-sulfatoethyl)-aniline, N,N-bis-($\beta$-hydroxyethyl)-2methoxy-5-chloroaniline, N-($\beta$-sulfatoethyl)-2,5-dimethoxyaniline, N-($\beta$-sulfatoethyl)-2-chloroaniline, acetoacetyl-2-naphthylamide-5-sulfonic acid, N-acetoacetylaniline-3- or -4-sulfonic acid, N-acetoacetyl-2-methoxy-5-sulfoaniline, N-acetoacetyl-4-methoxy-3-sulfoaniline, N-acetoacetyl-2-methoxy-5-methyl-4-sulfoaniline, N-acetoacetyl-2,5-dimethoxy-4-sulfoaniline, N-acetoacetyl-2-methoxy-5-methyl-4-($\beta$-sulfatoethylsulfonyl)aniline, N-acetoacetyl-2,5-dimethoxy-4-($\beta$-sulfatoethylsulfonyl)aniline, N-acetoacetyl-2-methoxy-5-($\beta$-sulfatoethylsulfonyl)aniline, N-acetoacetyl-4-($\beta$-sulfatoethylsulfonyl)aniline, N-acetoacetyl-3-($\beta$-sulfatoethylsulfonyl)aniline, 1-(4'-$\beta$-sulfatoethylsulfonylphenyl)-3-methyl-5-pyrazolone, 1-(4'-$\beta$-sulfatoethylsulfonylphenyl)-3-carboxy-5-pyrazolone, 1-(4'-sulfophenyl)-3-methyl-5-pyrazolone, 1-(4'-sulfophenyl)-3-carboxy-5-pyrazolone, 1-(2'-chloro-5'-sulfophenyl)-3-methyl- or -3-carboxy-5-pyrazolone, 1-(3'-sulfophenyl)-3-carboxy-5-pyrazolone, 1-(2'-methoxy-4'-sulfophenyl)-3-carboxy-5-pyrazolone, 1-(3'-sulfophenyl)-3-methyl-5aminopyrazole, 1-(4'-sulfophenyl)-3-methyl-5-aminopyrazole, 1-(2'-methoxy-5'-sulfophenyl)-3-methyl-5-aminopyrazole, 1-(2'-methoxy-5'-methyl-4'-sulfophenyl)-3-methyl-5-aminopyrazole, 1-(2'-chloro-5'-sulfophenyl)-3-methyl-5-aminopyrazole, 1-(3'-amino-4,-sulfophenyl)-3-carbethoxy-5-pyrazolone, 1-(4'-$\beta$-sulfatoethylsulfonylphenyl)-3-carboxy-5-pyrazolone, 2-N-methylamino-8-naphthol-6-sulfonic acid, 3-carboxy-5-pyrazolone, 1-phenyl-3-carboxy-5-pyrazolone, 1-(4,-nitrophenyl)-3-carboxy-5-pyrazolone, 1-(3,-acetylaminophenyl)-3-carboxy-5-pyrazolone, 1-(3'-carboxyphenyl)-3-methyl-5-pyrazolone, 2-hydroxy-3-carboxynaphthalene, 2-hydroxy-6-carboxynaphthalene, 8-hydroxyquinoline-5-sulfonic acid, 1,4-dimethyl-2-hydroxy-6-pyridone-5-sulfonic acid, N-sulfomethylaniline, 3-acetylamino-5-naphthol-7-sulfonic acid, 2-methylamino-8-naphthol-6-sulfonic acid, 2,5-disulfodiphenylamine, 4-sulfodiphenylamine, 1-[4'-chloro-6'-(4''-$\beta$-sulfatoethylsulfonylphenyl) amino-1',3',5'-triazin-2'-yl]amino-8-naphthol-3,6-disulfonic acid, 1-[4'-chloro-6'-(4''-$\beta$-sulfatoethylsulfonylphenyl)amino-1,,3,,5,-triazin-2,-yl]amino-8-naphthol-4,6-disulfonic acid, 2-[4'-chloro-6'-(4''-$\beta$-sulfatoethylsulfonylphenyl) amino-1',3',5'-triazin-2,-yl]-amino-8-naphthol-6-sulfonic acid, 3-[4,-chloro-6'-(4''-$\beta$-sulfatoethylsulfonylphenyl)amino-1,,3,,5,-triazin-2'-yl]amino-8-naphthol-3,6-disulfonicacid, 1-(4,-chloro-6'-methoxy-1',3',5'-triazin-2'-yl) amino-8-naphthol-3,6-disulfonic acid, 1-(4'-chloro-6'-methoxy-1',3',5'-triazin-2'-yl) amino-8-naphthol-4,6-disulfonic acid, 2-(4'-chloro-6,-methoxy-1',3',5'-triazin-2,-yl) amino-8-naphthol-6-sulfonic acid, 3-(4,-chloro-6,-methoxy-1',3',5'-triazin-2,-yl)amino-8-naphthol-6-sulfonic acid, 1-[4'-fluoro-6'-(4''-$\beta$-sulfatoethylsulfonylphenyl)amino-8-naphthol-3,6-disulfonic acid, 1-[4'-fluoro-6'-(4''-$\beta$-sulfatoethylsulfonylphenyl) amino-1',3',5'-triazin-2'yl]amino-8-naphthol-4,6-disulfonic acid, 2-[4'-fluoro-6'-(4''-$\beta$-sulfatoethylsulfonylphenyl) amino-1',3',5'-triazin-2'-yl]amino-8-naphthol-6-sulfonic acid, 3-[4'-fluoro-6'-(4''-$\beta$-sulfatoethylsulfonylphenyl) amino-1',3',5'-triazin-2'-yl]amino-8-naphthol-6-sulfonic acid, 1-(4,-$\beta$-sulfatoethylsulfonylbenzoyl) amino-8-naphthol-3,6-disulfonic acid or -4,6-disulfonic acid, 2- or 3-(4'-$\beta$-sulfatoethylsulfonylbenzoyl) amino-8-naphthol-6-sulfonic acid, 1-{4'-chloro-6,-[$\beta$-(4''-$\beta$''-sulfatoethylsulfonylphenyl) ethyl]-1',3',5'-triazin-2,-yl}amino-8-naphthol-3,6- or -4,6-disulfonic acid, 1-{4'-chloro-6'-[$\beta$-(3''-$\beta$''-sulfatoethyl-sulfonylphenyl) ethyl]-1',3',5'-triazin-2'-yl}amino-8-naphthol-3,6- or -4,6-disulfonic acid, 1-{4'-chloro-6'-{$\beta$-(4''-sulfophenyl)ethyl]-1',3',5'-triazin-2'-yl}amino-8-naphthol-3,6- or -4,6-disulfonic acid, 1-{4'-chloro-6,-{$\beta$-(2'',5''-disulfophenyl)ethyl]-1',3',5'-triazin-2'-yl}amino-8-naphthol-3,6- or -4,6-disulfonic acid, 1-{4'-fluoro-6,-{$\beta$-(3'',5''-disulfophenyl) ethyl]-1',3',5'-triazin-2,-yl}amino-8-naphthol-3,6- or -4,6-disulfonic acid, 1-($\beta$-hydroxyethyl)-4-methyl-6-hydroxy-2-pyridone, 1-($\beta$-hydroxyethyl)-3-cyano-4-methyl-6-hydroxy-2-pyridone, 1-($\beta$-hydroxyethyl)-3-carbamoyl-4-methyl-6-hydroxy-2-pyridone, 1-($\beta$-hydroxyethyl)-4-methyl-6-hydroxy-2-pyridone-3-sulfonic acid, 1-($\beta$-sulfatoethyl)-4-methyl-6-hydroxy-2-pyridone, 1-($\beta$-sulfatoethyl)-3-cyano-4-methyl-6-hydroxy-2-pyridone, 1-($\beta$-sulfatoethyl)-3-carbamoyl-4-methyl-6-hydroxy-2- pyridone, 1-(β-sulfatoethyl)-4-methyl-6-hydroxy-2-pyridone-3-sulfonic acid, 1-(β-sulfatoethyl)-4-methyl-6-hydroxy-2-pyridone, 1-(β-sulfatoethyl)-3-carbamoyl-4-methyl-6-hydroxy-2-pyridone, 1-(β-sulfatoethyl)-4-methyl-6-hydroxy-2-pyridone-3-sulfonic acid, 1-carboxymethyl-4-methyl-6-hydroxy-2-pyridone, 1-carboxymethyl-3-cyano-4-methyl-6-hydroxy-2-pyridone, 1-carboxymethyl-3-carbamoyl-4-methyl-6-hydroxy-2-pyridone, 1-carboxymethyl-4-methyl-6-hydroxy-2-pyridone-3-sulfonic acid, 1-(β-carboxyethyl)-4-methyl-6-hydroxy-2-pyridone, 1-(β-carboxyethyl)-3-cyano-4-methyl-6-hydroxy-2-pyridone, 1-(β-carboxyethyl)-3-carbamoyl-4-methyl-6-hydroxy-2-pyridone, 1-(β-carboxyethyl)-4-methyl-6-hydroxy-2-pyridone-2-sulfonic acid, 1-(β-acetylaminoethyl)-4-methyl-6-hydroxy-2-pyridone, 1-(β-acetylaminoethyl)-3-cyano-4-methyl-6-hydroxy-2-pyridone, 1-(β-acetylaminoethyl)-3-carbamoyl-4-methyl-6-hydrox-y-2-pyridone, 1-(β-acetylaminoethyl)-4-methyl-6-hydroxy-2-pyridone-3-sulfonic acid, 1-(β-acetylaminopropyl)-4-methyl-6-hydroxy-2-pyridone, 1-(β-acetylaminopropyl)-3-cyano-4-methyl-6-hydroxy-2-pyridone, 1-(β-acetylaminopropyl)-3-carbamoyl-4-methyl-6-hydroxy-2-pyridone, 1-(β-acetylaminopropyl)-4-methyl-6-hydroxy-2-pyridone-3-sulfonic acid, 4-hydroxy-2-quinoline, 1-amino-8-hydroxy-2-(phenylazo)naphthalene-3,6-disulfonic acid, 1-amino-8-hydroxy-2-(4,-sulfophenylazo)naphthalene-3,6-disulfonic acid, 1-amino-8-hydroxy-2-(2',5,-disulfophenylazo)naphthalene-3,6-disulfonic acid, 1-(β-aminoethyl)-3-cyano-4-methyl-6-hydroxy-2-pyridone, 1-(β-aminopropyl)-3-sulfomethyl-4-methyl-6-hydroxy-2-pyridone, 1,3-diaminobenzene, 1-amino-3-(N,N-di-β-hydroxyethylamino)benzene, 1-amino-3-(N,N-di-β-sulfatoethylamino)benzene, 1-amino-(3-N,N-di-β-hydroxyethylamino)-4-methoxybenzene, 1-amino-3-(N,N-di-β-sulfatoethylamino)-4-methoxybenzene, 1-amino-3-(sulfobenzylamino)benzene, 1-amino-3-(sulfobenzylamino)-4-chlorobenzene, 1-amino-3-(N,N-disulfobenzylamino)benzene, 1-hydroxy-3- or -4-methylbenzene, 1-hydroxybenzene-4sulfonic acid, 1-hydroxynaphthalene, 2-hydroxynaphthalene, 2-hydroxynaphthalene-6- or -7-sulfonic acid, 1-hydroxynaphthalene-4,7-disulfonic acid, 1-amino-3-methylbenzene, 1-amino-2-methoxy-5-methylbenzene, 1-amino-2,5-dimethylbenzene, 3-aminophenylurea, 1-amino-3-acetylaminobenzene, 1-amino-3-(hydroxyacetylamino)benzene,1,3-diaminobenzene-4-sulfonic acid, 1-aminonaphthalene-6- or -8-sulfonicacid, 1-amino-2-methoxynaphthalene-6-sulfonic acid, 2-aminonaphthalene-5,7-disulfonic acid, 1-amino-8-hydroxynaphthalene-6-sulfonic acid, 2-hydroxy-3-aminonaphthalene-5,7-disulfonic acid, 1-amino-8-hydroxynaphthalene-2,4,6-trisulfonic acid, 1-hydroxy-8-acetylaminonaphthalene-3-sulfonic acid, 1-benzoylamino-8-hydroxynaphthalene-3,6- or -4,6-disulfonic acid, 2-benzoylamino-5-hydroxynaphthalene-7-sulfonic acid, 2-methyl- and 2-ethylamino-5-hydroxynaphthalene-7-sulfonic acid, 2-(N-acetyl-N-methylamino)-5-hydroxynaphthalene-7-sulfonic acid, 2-ethylamino-8-hydroxynaphthalene-6-sulfonic acid, 2-acetylamino-8-hydroxynaphthalene-6-sulfonic acid, 1-(4,-aminobenzoylamino)-8-hydroxynaphthalene-3,6- and -4,6-disulfonic acid, 1-(4,-nitrobenzoylamino)-8-hydroxynaphthalene-3,6- and -4,6-disulfonic acid, 1-(3,-aminobenzoylamino)-6-hydroxynaphthalene-3,6- and -4,6-disulfonic acid, 1-(3,-nitrobenzoylamino)-8-hydroxynaphthalene-3,6- and -4,6-disulfonic acid, 2-(4'-amino-3'-sulfophenyl)amino-5-hydroxynaphthalene-7-sulfonic acid, 3-methyl-5-pyrazolone, 1-phenyl-3-methyl-5-pyrazolone, 1-(3,-aminophenyl)-3-methyl-5-pyrazolone, 1-(2',5,-disulfophenyl)-3-methyl-5pyrazolone, 1-(2'-methyl-4'-sulfophenyl)-5-pyrazolone-3-carboxylic acid, 1-(4',8'-disulfonaphthyl-2,-yl)-3-methyl-5-pyrazolone, 1-(5',7,-disulfonaphthyl-2-)-3-methyl-5-pyrazolone, 1-(2',5,-dichloro-4,-sulfophenyl)-3-methyl-5-pyrazolone, 3-aminocarbonyl-4-methyl-6-hydroxy-2-pyridone, 1-ethyl-3-cyano- or -3-chloro-4-methyl-6-hydroxy-2-pyridone, 1-ethyl-3-sulfomethyl-4-methyl-6-hydroxy-2-pyridone, 2,4,6-triamino-3-cyanopyridine, 2-(3,-sulfophenyl)-amino-4,6-diamino-3-cyanopyridine, 2-(2'-hydroxyethylamino)-3-cyano-4-methyl-6-aminopyridine, 2,6-bis-(2,-hydroxyethylamino)-3-cyano-4-methylpyridine, 1-ethyl-3-carbamoyl-4-methyl-6-hydroxy-2-pyridone, 1-ethyl-3-sulfomethyl-4-methyl-5-carbamoyl-6-hydroxy-2-pyridone, N-acetoacetylaminobenzene, 5-acetylamino-2-sulfoaniline.

The compounds of the general formula (5) usable according to the invention for the synthesis of the azo compounds (1) according to the invention are hitherto unknown. The invention accordingly also relates to these compounds, processes for their preparation and their use for the synthesis of dyes, such as, in particular, to give the azo compounds (1) according to the invention. They can be prepared analogously to the known procedures of the reaction of acid chlorides with amines by first reacting a compound of the general formula (6)

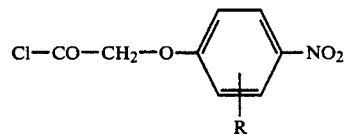

(6)

in which R has the abovementioned meaning with an amino compound of the formula

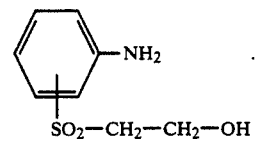

(7)

The reaction is carried out in solvents or diluents customary and suitable for this type of reaction and in the presence of an acid-binding agent, as a rule, at a temperature between 50° and 80° C. Examples of suitable solvents are water or an organic solvent or diluent or a mixture of water and a water-miscible organic solvent. Examples of organic solvents or diluents are alkanols of 1 to 6 carbon atoms, preferably 1 to 4 carbon atoms, such as, for example, methanol, dioxane, toluene, the xylenes, chlorobenzene, o-dichlorobenzene, m-dichlorobenzene, dimethylformamide and N-methylpyrrolidone. Examples of acid-binding agents are potassium carbonate, magnesium oxide, sodium carbonate, sodium hydroxide, triethylamine and triethanolamine. In aqueous medium, a pH between 6 and 12, preferably between 8 and 10, is maintained.

Examples of acid chlorides of the general formula (6) are 4-nitrophenoxyacetyl chloride, 2,4-dinitrophenoxyacetyl chloride, 2-chloro-4-nitrophenoxyacetyl chloride, 2-bromo-4-nitrophenoxyacetyl chloride, 2-methyl-4-nitrophenoxyacetyl chloride and 2-methoxy-4-nitrophenoxyacetyl chloride.

Amino compounds of the general formula (7) are in particular 4-(β-hydroxyethylsulfonyl)aniline and 3-(β-hydroxyethylsulfonyl)aniline.

The carboxamide compounds according to the invention, which are obtainable in this manner according to the invention and are also new and have the general formula (8)

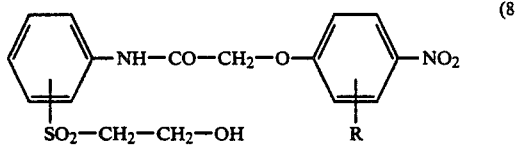

in which R has the abovementioned meaning are then, after being isolated from the reaction mixture for example by crystallization or by distilling off the solvent or by acidification and filtration, reduced analogously to known procedures to give the amino compound of the general formula (5), for example by catalytic hydrogenation using hydrogen on palladium, platinum or Raney nickel at a temperature between 50° and 110° C. and at elevated pressure or by Bechamp reduction using iron in acidic medium, for example using iron in ethanol/glacial acetic acid. The reduction can be carried out in a suitable solvent such as water, methanol or ethanol or a mixture thereof.

Not only the compounds of the general formula (1) but also the compounds of the general formula (5), in which Y and Y' are a β-hydroxyethyl group, can be converted in a conventional and known manner into compounds in which Y and Y' have a meaning different from that of a β-hydroxyethyl group, for example into their ester derivatives, such as, for example, of polybasic inorganic acids or of aliphatic and aromatic carboxylic or sulfonic acids, for example into compounds in which Y and Y' are a β-chloroethyl, β-sulfatoethyl, β-phosphatoethyl, β-thiosulfatoethyl, β-acetyloxyethyl or β-toluenesulfonyloxyethyl group. Examples of suitable esterification and acylating agents are the corresponding inorganic or organic acids or their anhydrides or halides or amides, such as, for example, sulfuric acid, sulfuric acid containing sulfur trioxide, chlorosulfonic acid, sulfamic acid, phosphoric acid, phosphorus oxychloride, mixtures of phosphoric acid and phosphorus pentoxide, acetic anhydride, toluenesulfonyl chloride and thionyl chloride.

Those compounds in which Y and Y' are a vinyl group can be prepared from their analogous ester derivatives by means of alkali, for example in aqueous medium at a pH of 10 to 12 and a temperature between 40° and 50° C. and a reaction time of 10 to 20 minutes. The synthesis of, for example, β-(dialkylamino)ethylsulfonyl and β-thio-sulfatoethylsulfonyl derivatives of the compounds (1) and (5) is carried out by reaction of their vinylsulfonyl compounds with the corresponding dialkylamine or with an alkali metal salt of thiosulfuric acid, such as sodium thiosulfate. All these procedures of converting one group —SO$_2$—Y or —SO$_2$—Y' into another are known to one skilled in this field of fiber-reactive dyes and are described in the literature in large numbers.

The compounds according to the invention of the general formula (1)—hereinafter designated as compounds (1)—have fiber-reactive properties and have very valuable dye properties. They can therefore be used for the dyeing (including printing) of hydroxy-containing and/or carboxamido-containing materials. For this purpose, the solutions formed in the synthesis of the compounds (1), if desired after the addition of a buffer substance and if also desired after concentration, can be used directly as liquid preparation for dyeing.

The compounds (1) can be precipitated and isolated from the aqueous synthesis solutions by generally known methods for water-soluble compounds, for example by precipitation from the reaction medium by means of an electrolyte, such as, for example, sodium chloride or potassium chloride, or, alternatively, by evaporation of the reaction solution itself, for example by spray-drying. If the last-mentioned type of isolation is chosen, it is in many cases advisable to remove any amounts of sulfate present in the solutions, before the evaporation, by precipitation as calcium sulfate and separation by filtration.

The present invention accordingly also relates to the use of the compounds (1) for the dyeing (including printing) of hydroxy—and/or carboxamido-containing materials and to processes for applying them to these substrates. The materials are preferably used in the form of fiber materials, in particular in the form of textile fibers, such as yarns, wound articles and fabrics. This is done analogously to known procedures.

Hydroxy-containing materials are those of natural or synthetic origin, such as, for example, cellulose fiber materials or their regenerated products and polyvinyl alcohols. Cellulose fiber materials are preferably cotton, but also other vegetable fibers, such as linen, hemp, jute and ramie fibers; examples of regenerated cellulose fibers are staple viscose and filament viscose.

Examples of carboxamido-containing materials are synthetic and natural polyamides and polyurethanes, in particular in the form of fibers, for example wool and other animal hair, silk, leather, nylon-6,6, nylon-6, nylon-11 and nylon-4.

The compounds (1) can be applied and fixed, in accordance with the use according to the invention, on the substrates mentioned, in particular on the fiber materials mentioned, by the application techniques known for watersoluble, fiber-reactive dyes, for example by applying the compound (1) in dissolved form to the substrate or incorporating it therein and fixing it on it or in it, if necessary by applying heat and/or if necessary by applying an alkaline agent. These dyeing and fixation procedures have been described in the literature in large numbers (see, for example, European patent application No. 0,181,585 A2).

The dyeings according to the invention have good light fastness properties, in particular on cellulose fiber materials, not only in dry conditions but also in wet conditions, for example moistened with a perspiration solution, and also good wet fastness properties, such as, for example, good wash fastness at 60 to 95° C., also in the presence of perborates, good acid and alkaline milling, cross-dyeing and perspiration fastness properties, high resistance to steam, good alkali, acid, water and sea water fastness, furthermore good pleating fastness, hot press fastness and rub fastness. Likewise they have good acid fading resistance upon storage of moist dyed material still containing acetic acid.

The Examples which follow serve to illustrate the invention. Parts and percentages are by weight, unless stated otherwise. Parts by weight relate to parts by volume as the kilogram relates to the liter.

The compounds described in these Examples by way of their formulae are given in the form of the free acids;

in general, they are prepared and isolated in the form of their alkali metal salts, such as lithium salts, sodium salts or potassium salts, and used for dyeing in the form of their salts. Likewise, the starting compounds and components mentioned in the Examples below, in particular the Table Examples, in the form of the free acids, can be used in the synthesis as such or in the form of their salts, preferably their alkali metal salts.

The absorption maxima ($\lambda_{max}$) given for the compounds according to the invention in the visible region were determined using their alkali metal salts in aqueous solution. In the Table Examples, the $\lambda_{max}$ values are written in parentheses next to the hue; the wavelengths are given in nm.

Example A

A solution of 243 parts of 4-nitrophenoxyacetyl chloride in 500 parts by volume of toluene is slowly added with thorough stirring to a solution of 206 parts of 4-($\beta$-hydroxyethylsulfonyl)aniline in about 1500 parts of water of a pH of 9 at 5° to 10° C., while maintaining a pH of 9 by means of about 3250 parts of a 20% aqueous sodium carbonate solution. Stirring of the mixture at 5° to 10° C. is continued for about 2 hours and then at 20° C. for another 16 hours, unreacted aniline is dissolved by the addition of 4000 parts by volume of aqueous 5N hydrochloric acid, the undissolved product is filtered off with suction and recrystallized from methanol. It has the formula

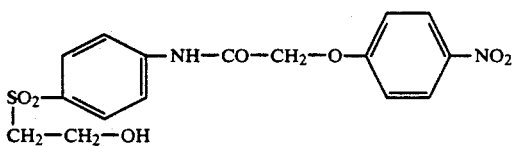

and the following physical data:
Melting point: 220° C.;
Bands in the IR spectrum: 3538 cm$^{-1}$ (OH); 3376 cm$^{-1}$ (NH); 2952 cm$^{-1}$ (CH); 1696 cm$^{-1}$ (CO).

EXAMPLE B 50 parts of the nitro compound from Example A are suspended in 300 parts of methanol and reduced at a temperature of 60° C. and a hydrogen pressure of 60 bar on Raney nickel by means of hydrogen. After the end of the reaction, the catalyst is removed at 70° C. by filtration, and the filtrate is cooled to 20° C. The crystallized product is filtered off with suction. It has the formula

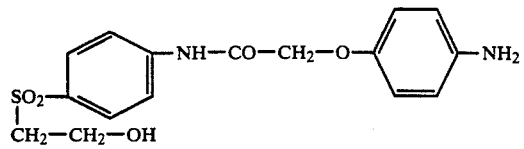

and the following physical data:
Melting point: 158° C.;
Bands in the IR spectrum: 3352 cm$^{-1}$ (NH); 3290 cm$^{-1}$ (NH); 2912 cm$^{-1}$ (CH); 1680 cm$^{-1}$ (CO).

EXAMPLE C 30 parts of the aniline compound from Example B are stirred into 120 parts of sulfuric acid monohydrate at 10° C. The resulting suspension is then slowly warmed to 20° C., stirred for another 16 hours, then poured onto 1600 parts of ice, and the precipitate is filtered off with suction. The compound has the formula

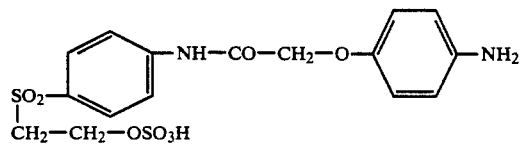

and a melting point of more than 300° C. and shows the following bands in the IR spectrum: 3424 cm$^{-1}$ (NH); 3352 cm$^{-1}$ (NH); 2928 cm$^{-1}$ (CH); 1695 cm$^{-1}$ (CO).

EXAMPLE 1

11 parts of an aqueous 5N sodium nitrite solution are first added to an aqueous solution of 21.5 parts of the aniline compound from Example C in 3000 parts of water of a pH of 6.9, and the mixture is then added at 5° C. to 30 parts of aqueous concentrated hydrochloric acid. Stirring is continued for one hour, and excess nitrite is removed by means of sulfamic acid. While maintaining a pH of 6.5, 15 parts of 6-sulfo-2-acetylamino-8-naphthol are then added at 5° C. to the diazonium salt suspension, and the mixture is then stirred at 15° to 20° C. for another three hours, the pH is brought to 4.5 to 5, and the azo compound according to the invention is isolated by salting out with sodium chloride and filtration.

Written in the form of the free acid, it has the formula

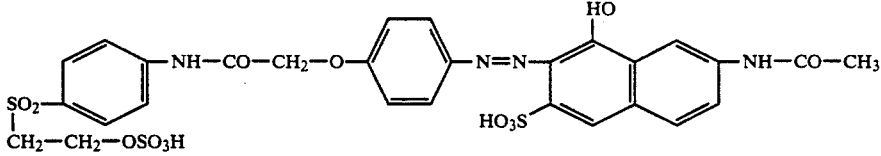

($\lambda_{max}$ = 509 nm)

and has very good fiber-reactive dye properties. Using the application and fixation processes known for fiber-reactive dyes, red dyeings and prints which have high color strength and good fastness properties are obtained on the materials mentioned in the description, such as, in particular, cellulose fiber materials, for example cotton, by means of the azo compound according to the invention.

EXAMPLES 2 TO 25

Further azo compounds according to the invention of the general formula (A)

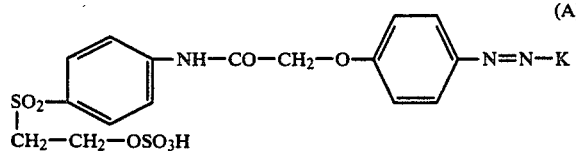

are described in the Table Examples below by means of their coupling component H—K. They can be prepared by the procedure according to the invention, for example analogously to Example 1 above, and likewise have very good fiber-reactive dye properties. They produce dyeings and prints of high color strength on the materials mentioned in the description, such as, in particular cellulose fiber materials, by the application and fixation methods customary for fiber-reactive dyes in the hue given in the particular Table Example (in this case on cotton) which have good fastness properties.

| Ex. | Coupling component H-K in formula (A) | Hue |
|---|---|---|
| 2 | 6-Sulfo-3-benzoylamino-8-naphthol | Red |
| 3 | 1-(4'-β-Sulfatoethysulfonylphenyl)-3-methyl-5-pyrazolone | Yellow (416) |
| 4 | 4,6-Disulfo-1-acetylamino-8-naphthol | Bluish red (546) |
| 5 | 3,6-Disulfo-2-aminonaphthalene | Red |
| 6 | 5,7-Disulfo-2-aminonaphthalene | Navy |
| 7 | 4-Sulfo-1-naphthol | Red |
| 8 | 3,6-Disulfo-1-naphthol | Red |
| 9 | 1-(N-β-Sulfoethyl)-4-methyl-2-hydroxy-6-pyridone | Orange |
| 10 | 3,6,8-Trisulfo-2-aminonaphthalene | Red |
| 11 | 6-Sulfo-3-acetylamino-8-naphthol | Red (497) |
| 12 | N,N-Bis-(β-sulfatoethyl)aniline | Orange |
| 13 | N-Ethyl-N-(β-sulfatoethyl)aniline | Red |
| 14 | 6-Sulfo-2-acetylamino-8-naphthol | Red (509) |
| 15 | 3,6-Disulfo-1-benzoylamino-8-naphthol | Bluish red (523) |
| 16 | 4,6-Disulfo-1-benzoylamino-8-naphthol | Bluish red |
| 17 | N,N-Bis-(β-sulfatoethyl-3-chloro-aniline | Orange |
| 18 | 5-Sulfo-1-naphthol | Red |
| 19 | 3,6-Disulfo-1-amino-2-{2'-sulfo-5'-[5"-(β-sulfatoethylsulfonyl)-1",2",3"-benzotriazol-1"'-yl]phenyldiazolyl}-8-naphthol | Greenish blue |
| 20 | 3,6-Disulfo-1-amino-2-[4'-(β-sulfatoethylsulfonyl)phenyldiazolyl]-8-naphthol | Greenish blue (625) |
| 21 | 6-Sulfo-2-methylamino-8-naphthol | Red |
| 22 | 4-Sulfodiphenylamine | Red |
| 23 | 5-Sulfo-2-acetylamino-7-naphthol | Red |
| 24 | 3,6-Disulfo-2-acetylamino-8-naphthol | Red |
| 25 | 2,4-Disulfo-1-amino-8-naphthol | Blue |
| 26 | 3,6-Disulfo-1-amino-8-naphthol (coupled in the 7-position) | Blue |
| 27 | 4,6-Disulfo-1-amino-8-naphthol (coupled in the 7-position) | Blue |
| 28 | 3,6-Disulfo-1-phenylureido-8-naphthol | Blue |
| 29 | 3-Sulfo-1-naphthol | Red |
| 30 | 5-Sulfo-2-naphthol | Red |
| 31 | 6-Sulfo-2-naphthol | Bluish red |
| 32 | 8-Sulfo-2-naphthol | Bluish red |
| 33 | 3,6-Disulfo-1-acetylamino-8-naphthol | Blue |
| 34 | N,N-Bis-(β-hydroxyethyl)aniline | Red |
| 35 | 3,6,8-Trisulfo-1-naphthol | Bluish red |
| 36 | 3,6-Disulfo-2-naphthol | Red |
| 37 | 3,6-Disulfo-1-acetylamino-8-naphthol | Blue |
| 38 | 4,6-Disulfo-1-acetylamino-8-naphthol | Blue |
| 39 | N-Ethyl-N-(3'-sulfobenzyl)aniline | Red |
| 40 | 5-Sulfo-1,4-dimethyl-2-hydroxy-6-pyridone | Yellow |
| 41 | 2-Carboxyacetoacetylaniline | Yellow |
| 42 | 5-Sulfo-8-hydroxyquinoline | Red |
| 43 | 3-Sulfoacetoacetylaniline | Yellow |
| 44 | 1-(4'-Sulfophenyl)-3-methyl-5-pyrazolone | Yellow (413) |
| 45 | 1-(2'-Chloro-5'-sulfophenyl)-3-methyl-5-pyrazolone | Yellow |
| 46 | 1-(2,5-Disulfophenyl)-3-methyl-5-pyrazolone | Yellow |
| 47 | 1-(4',8'-Disulfonaphth-2'-yl)-3-methyl-5-pyrazolone | Yellow |
| 48 | 1-(4'-Sulfophenyl)-3-methyl-5-aminopyrazole | Yellow |
| 49 | 3,6-Disulfo-1-[4'-chloro-6'-(3"-sulfophenyl)amino-1',3',5'-triazin-2'-yl]-amino-8-naphthyl | Bluish red |
| 50 | 3,6-Disulfo-1-{4'-chloro-6'-[4"-(β-sulfatoethylsulfonyl)phenyl]amino-1',3',5'-triazin-2'-yl}amino-8-naphthol | Bluish red (529) |
| 51 | 6,8-Disulfo-2-naphthol | Red |
| 52 | 6-Sulfo-2-benzoylamino-8-naphthol | Red |
| 53 | N-Acetoacetyl-(2-methoxy-5-methyl-4-sulfo)aniline | Yellow |
| 54 | 1-(4'-Sulfophenyl)-3-carboxy-5-pyrazolone | Yellow |
| 55 | 5-Acetylamino-2-sulfoaniline | Yellow |

EXAMPLES 56 TO 109

Further azo compounds according to the invention written in the form of the free acids of the general formula (B)

$$SO_2\text{-}\bigcirc\text{-}NH\text{-}CO\text{-}CH_2\text{-}O\text{-}\bigcirc\text{-}N=N\text{-}K \quad (B)$$
$$|$$
$$CH_2$$
$$|$$
$$CH_2\text{-}OSO_3H$$

are described in the Table Examples below by means of their coupling component H-K. They can be prepared by the procedure according to the invention, for example analogously to Example 1 above, and likewise have very good fiber-reactive dye properties. They produce dyeings and prints of high color strength on the materials mentioned in the description, such as, in particular cellulose fiber materials, by the application and fixation methods customary for fiber-reactive dyes in the hue given in the particular Table Example (in this case on cotton) which have goof fastness properties.

| Ex. | Coupling component H-K in formula (B) | Hue |
|---|---|---|
| 56 | 6-Sulfo-3-benzoylamino-8-naphthol | Red |
| 57 | 1-(4'-β-Sulfatoethylsulfonylphenyl)-3-methyl-5-pyrazolone | Yellow (410) |
| 58 | 4,6-Disulfo-1-acetylamino-8-naphthol | Bluish red (508) |
| 59 | 3,6-Disulfo-2-aminonaphthalene | Red |
| 60 | 5,7-Disulfo-2-aminonaphthalene | Navy |
| 61 | 4-Sulfo-1-naphthol | Red |
| 62 | 3,6-Disulfo-1-naphthol | Red |
| 63 | 1-(N-β-Sulfoethyl)-4-methyl-2-hydroxy-6-pyridone | Orange |
| 64 | 3,6,8-Trisulfo-2-aminonaphthalene | Red |
| 65 | 6-Sulfo-3-acetylamino-8-naphthol | Red (498) |
| 66 | N,N-Bis-(β-Sulfatoethyl)aniline | Orange |
| 67 | N-Ethyl-N-(β-sulfatoethyl)aniline | Red |
| 68 | 6-Sulfo-2-acetylamino-8-naphthol | Red (509) |
| 69 | 3,6-Disulfo-1-benzoylamino-8-naphthol | Bluish red |

-continued

| Ex. | Coupling component H-K in formula (B) | Hue |
|---|---|---|
| 70 | 4,6-Disulfo-1-benzoylamino-8-naphthol | Bluish red (523) |
| 71 | N,N-Bis-(β-Sulfatoethyl)-3-chloro-aniline | Orange |
| 72 | 5-Sulfo-1-naphthol | Red |
| 73 | 3,6-Disulfo-1-amino-2-{2'-sulfo-5'-[5''-(β-sulfatoethylsulfonyl)-1'',2'',3''-benzotriazol-1''-yl]-phenyldiazo}-8-naphthol | Greenish blue |
| 74 | 3,6-Disulfo-1-amino-2-[4'-(β-sulfatoethylsulfonyl)phenyldiazo]-8-naphthol | Greenish blue (625) |
| 75 | 6-Sulfo-2-methylamino-8-naphthol | Red |
| 76 | 4-Sulfodiphenylamine | Red |
| 77 | 5-Sulfo-2-acetylamino-7-naphthol | Red |
| 78 | 3,6-Disulfo-2-acetylamino-8-naphthol | Red |
| 79 | 2,4-Disulfo-1-amino-8-naphthol | Blue |
| 80 | 3,6-Disulfo-1-amino-8-naphthol (coupled in the 7-position) | Blue |
| 81 | 4,6-Disulfo-1-amino-8-naphthol (coupled in the 7-position) | Blue |
| 82 | 3,6-Disulfo-1-phenylureido-8-naphthol | Blue |
| 83 | 3-Sulfo-1-naphthol | Red |
| 84 | 5-Sulfo-2-naphthol | Red |
| 85 | 6-Sulfo-2-naphthol | Bluish red |
| 86 | 8-Sulfo-2-naphthol | Bluish red |
| 87 | 3,6-Disulfo-1-acetylamino-8-naphthol | Blue |
| 88 | N,N-Bis-(β-hydroxyethyl)aniline | Red |
| 89 | 3,6,8-Trisulfo-1-naphthol | Bluish red |
| 90 | 3,6-Disulfo-2-naphthol | Red |
| 91 | 3,6-Disulfo-1-acetylamino-8-naphthol | Blue |
| 92 | 4,6-Disulfo-1-acetylamino-8-naphthol | Blue |
| 93 | N-Ethyl-N-(3'-sulfobenzyl)aniline | Red |
| 94 | 5-Sulfo-1,4-dimethyl-2-hydroxy-6-pyridone | Yellow |
| 95 | 2-Carboxyacetoacetylaniline | Yellow |
| 96 | 5-Sulfo-8-hydroxyquinoline | Red |
| 97 | 3-Sulfoacetoacetylaniline | Yellow |
| 98 | 1-(4'-Sulfophenyl)-3-methyl-5-pyrazolone | Yellow (414) |
| 99 | 1-(2'-Chloro-5'-sulfophenyl)-3-methyl-5-pyrazolone | Yellow |
| 100 | 1-(2',5'-Disulfophenyl)-3-methyl-5-pyrazolone | Yellow |
| 101 | 1-(4',8'-Disulfonaphth-2'-yl)-3-methyl-5-pyrazolone | Yellow |
| 102 | 1-(4'-Sulfophenyl)-3-methyl-5-amino-pyrazole | Yellow |
| 103 | 3,6-Disulfo-1-[4'-chloro-6'-(3''-sulfo-phenyl)amino-1',3',5'-triazin-2'-yl]-amino-8-naphthol | Bluish red |
| 104 | 3,6-Disulfo-1-{4'-chloro-6'-[4''-(β-sulfatoethylsulfonyl)phenyl]amino-1',3',5'-triazin-2'-yl}amino-8-naphthol | Bluish red (529) |
| 105 | 6,8-Disulfo-2-naphthol | Red |
| 106 | 6-Sulfo-2-benzoylamino-8-naphthol | Red |
| 107 | N-Acetoacetyl-(2-methoxy-5-methyl-4-sulfo)aniline | Yellow |
| 108 | 1-(4'-Sulfophenyl)-3-carboxy-5-pyrazolone | Yellow |
| 109 | 5-Acetylamino-2-sulfoaniline | Yellow |

We claim:

1. A water-soluble azo compound corresponding the formula

D—N═N—K in which:

D is a group of the formula

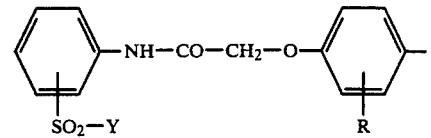

in which

Y is vinyl or a group of the formula —CH$_2$—CH$_2$—X in which X is a substituent which is eliminated by an alkali while forming the vinyl, and R is hydrogen, nitro, alkyl of 1 to 4 carbons, alkoxy of 1 to 4 carbons, carboxy, hydroxy or halogen;

K is a group of the formula

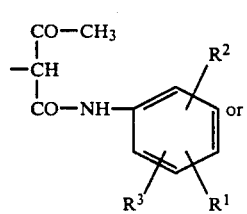

or

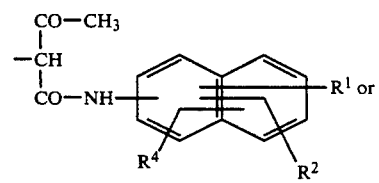

or

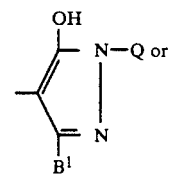

or

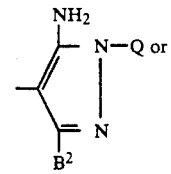

or

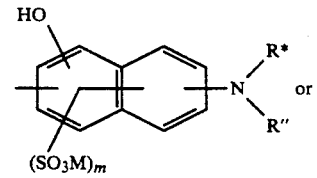

or

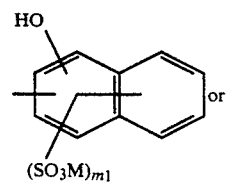

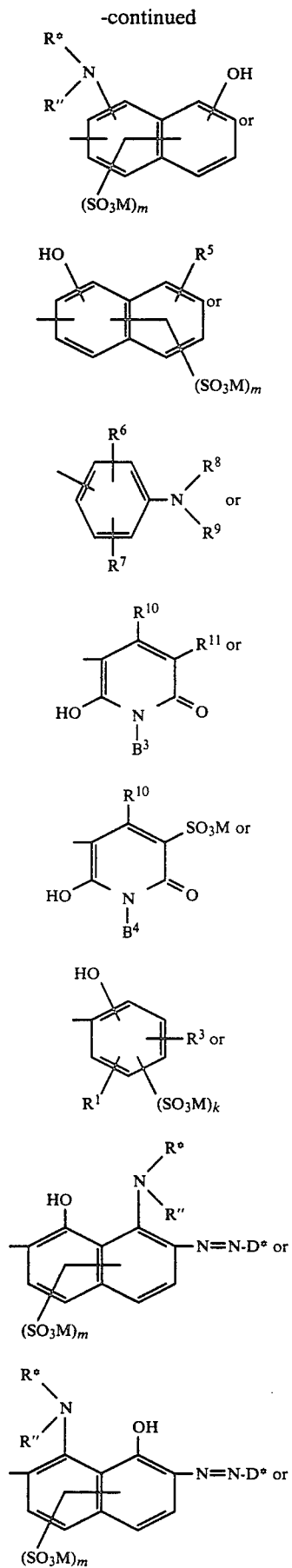
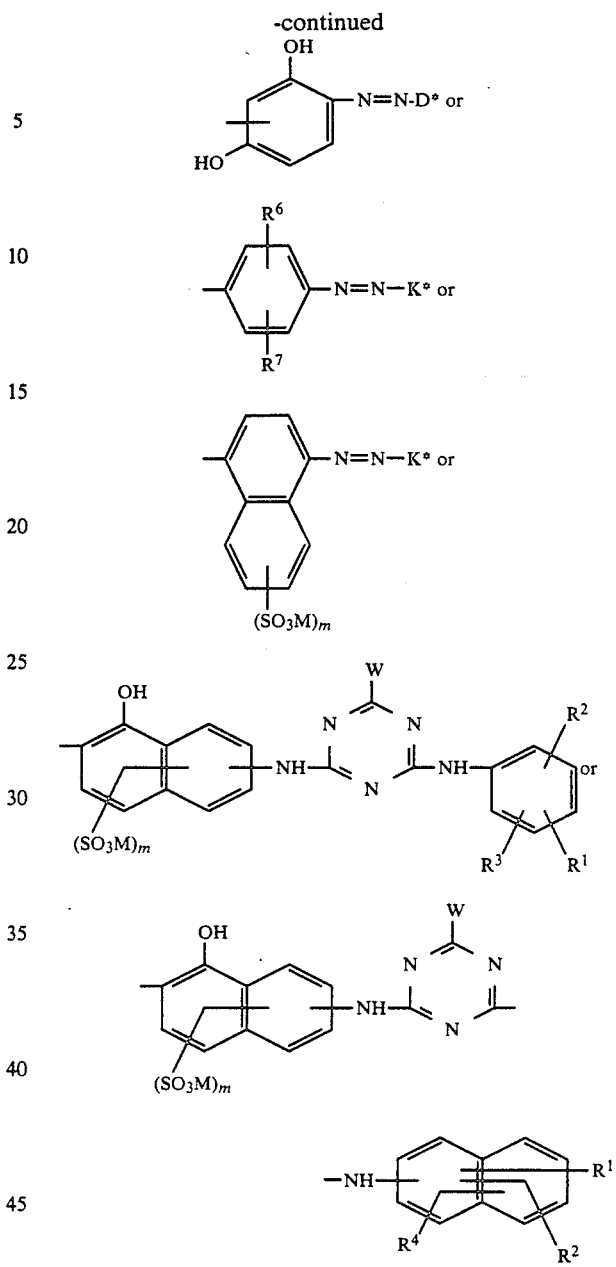

in which:

M is hydrogen or an alkali metal, $R^1$ is hydrogen, carboxy or sulfo, or a group of the formula $—SO_2—Y$ in which Y has one of the above meanings, $R^2$ is hydrogen, alkyl of 1 to 4 carbons, alkoxy of 1 to 4 carbons, chlorine, bromine, carboxy, sulfo or nitro, $R^3$ is hydrogen, alkyl of 1 to 4 carbons, alkoxy of 1 to 4 carbons, chlorine or bromine, $R^4$ is hydrogen, sulfo or carboxy, $B^1$ is alkyl of 1 to 4 carbons, carboxy, carbalkoxy of 2 to 5 carbons or carbamoyl, or is phenyl substituted by substituents selected from sulfo, carboxy, methyl, ethyl, methyoxy, ethoxy and chlorine, $B^2$ is alkyl of 1 to 4 carbons, carboxy, carbalkoxy of 2 to 5 carbons or carbamoyl, or is phenyl which is optionally substituted by 1 or 2 substituents selected from alkyl of 1 to 4 carbons, alkoxy of 1 to 4 carbons, chlorine, bromine and sulfo, Q is phenyl which is optionally substituted by 1, 2 or 3 substituents selected from chlorine, bromine, methyl, ethyl, methoxy, ethoxy, carboxy, sulfo, acetylamino and a group of the formula —SO$_2$—Y with Y having the above mentioned meaning, or is a naphthyl which is optionally substituted by 1, 2 or 3 sulfos or by an alkyl of 1 to 4 carbons, an alkoxy of 1 to 4 carbons, a chlorine or an alkanoylamino of 2 to 5 carbons, or by a group of the formula —SO$_2$—Y with Y having the above mentioned meaning, or is a naphthyl substituted by 1, 2 or 3 sulfos and by a substituent selected from alkyl of 1 to 4 carbons, alkoxy of 1 to 4 carbons, chlorine, alkanoylamino of 2 to 5 carbons and a group of the formula —SO$_2$—Y with Y having the above mentioned meaning, R* is hydrogen or alkyl of 1 to 4 carbons, which is optionally substituted by a phenyl which is further optionally substituted by sulfo or by —SO$_2$—Y or by sulfo and —SO$_2$—Y in which Y is defined as above, R" is hydrogen or alkyl of 1 to 4 carbons which is optionally substituted by phenyl or by a group of the formula —SO$_2$—Y with Y of the above mentioned meaning, or is phenyl which is optionally substituted by 1 or 2 substituents selected from alkyl of 1 to 4 carbons, alkoxy of 1 to 4 carbons, chlorine, bromine, sulfo and —SO$_2$—Y with Y of the above mentioned meaning, R$^5$ is phenylureido wherein the phenyl is optionally substituted by a group of the formula —SO$_2$—Y with Y of the above mentioned meaning, or is alkanoylamino of 2 to 5 carbons which is optionally substituted in the alkyl moiety by a group of the formula —SO$_2$—Y with Y of the above mentioned meaning, or is alkenoylamino of 3 to 5 carbons, or is benzoylamino which is optionally substituted by substituents selected rom chlorine, methyl, methoxy, nitro, sulfo, carboxy and a group of the formula —SO$_2$—Y with Y of the above mentioned meaning, R$^6$ is hydrogen, alkyl of 1 to 4 carbons, alkoxy of 1 to 4 carbons, sulfo, carboxy, carbalkoxy of 2 to 5 carbons, halogen or alkoxy of 1 to 4 carbons substituted by hydroxy, acetoxy, carboxy, carbamoyl, cyano or halogen, R$^7$ is hydrogen, alkyl of 1 to 4 carbons, alkoxy of 1 to 4 carbons, halogen, cyano, trifluoromethyl or alkoxy of 1 to 4 carbon atoms substituted by hydroxy, acetoxy, carboxy, carbamoyl, cyano, halogen or a group of the formula —SO$_2$—Y with Y of the above mentioned meaning, or is alkanoylamino of 2 to 5 carbons which is optionally substituted by chlorine, bromine, alkoxy of 1 to 4 carbons, phenoxy, phenyl, hydroxy, carboxy, sulfo or a group of the formula —SO$_2$—Y with Y of the above mentioned meaning, or is alkenoylamino of 3 to 5 carbons which is optionally substituted by chlorine, bormine, carboxy or sulfo, or is benzoylamino which is optionally substituted in the benzene ring by substituents selected from chlorine, methyl, sulfo and a group of the formula —SO$_2$—Y with Y of the abovementioned meanings, or is alkylsulfonyl of 1 to 4 carbons, or is phenylsulfonyl which is optionally substituted in the phenyl by substituents selected from chlorine, methyl, sulfo and a group of the formula —SO$_2$—Y with Y of the above mentioned meanings, or is alkylsulfonylamino of 1 to 4 carbons which is optionally substituted by hydroxy, sulfato, chlorine, bromine, alkoxy of 1 to 4 carbons or a group of the formula —SO$_2$—Y with Y of the above mentioned meanings, or is phenylsulfonylamino which is optionally substituted in the phenyl by substituents selected from chlorine, methyl, sulfo and a group of the formula —SO$_2$—Y with Y of the abovementioned meanings, or is carbamoyl which is optionally mono- or disubstituted on th nitrogen by one or two substituents selected from the group: alkyl of 1 to 4 carbons, alkyl of 1 to 4 carbons substituted by hydroxy, sulfo, carboxy, sulfato, phenyl or a group of the formula —SO$_2$—Y with Y of the above mentioned meanings, cycloalkyl of 5 to 8 carbons; phenyl; phenyl substituted by substituents selected from chlorine, sulfo, methyl, methoxy, carboxy and a group of the formula —SO$_2$—Y with Y of the above mentioned meanings; or is sulfamoyl which is optionally mono- or disubstituted on the nitrogen by one or two substituents selected from the group consisting of: alkyl of 1 to 4 carbons; alkyl of 1 to 4 carbons substituted by hydroxy, sulfo, carboxy, sulfato, phenyl or a group of the formula —SO$_2$—Y with Y of the above mentioned meanings; cycloalkyl of 5 to 8 carbons; phenyl; phenyl substituted by substituents selected from chlorine, sulfo, methyl, methoxy, carboxy and a group of the formula —SO$_2$—Y with Y of the above mentioned meanings; or is ureido which is optionally mono- or disubstituted on the terminal nitrogen by one or two substituents from the group consisting of: alkyl of 1 to 4 carbons; alkyl of 1 to 4 carbons substituted by substituents selected from hydroxy, sulfo, carboxy, sulfato, phenyl or a group of the formula —SO$_2$—Y with Y of the above mentioned meanings; cycloalkyl of 5 to 8 carbons; phenyl; phenyl substituted by substituents selected from the group consisting of chlorine, sulfo, methyl, methoxy, carboxy and a group of the formula —SO$_2$—Y with Y of the above mentioned meaning;

R$^8$ is hydrogen, alkyl of 1 to 4 carbons or alyl of 1 to 4 carbons substituted by hydroxy, sulfo, carboxy, sulfato, a group of the formula —SO$_2$—Y with Y of the above mentioned meanings or by phenyl, or is alkenyl of 2 to 4 carbons which is optionally substituted by carboxy, sulfo, chlorine or bromine, or is cycloalkyl of 5 to 8 carbons;

R$^9$ is hydrogen, alkyl of 1 to 4 carbons or alkyl of 1 to 4 carbons substituted by hydroxy, sulfo, carboxy, sulfato, phenyl or a group of the formula —SO$_2$—Y where Y has the above mentioned meanings, or is alkenyl of 2 to 5 carbons which is optionally substituted by carboxy, sulfo or a group of the formula —SO$_2$—Y with Y of the above mentioned meaning, or by chlorine or bromine, or is cycloalkyl of 5 to 8 carbon atoms, or is phenyl which is optionally substituted by substituents selected from chlorine, sulfo, methyl, methoxy, carboxy and a group of the formula —SO$_2$—Y of the above mentioned meanings, or R[8] and R[9] represent together with the nitrogen N-piperidino, N-morpholino or N-piperazino, R[10] is hydrogen, alkyl of 1 to 4 carbons or alkyl of 1 to 4 carbons substituted by alkoxy of 1 to 4 carbons or by cyano, R[11] is hydrogen, sulfo, sulfoalkyl with an alkyl moiety of 2 to 5 carbons, cyano or carbamoyl, B[3] is hydrogen or alkyl of 1 to 6 carbons which is optionally substituted by phenyl, sulfo, sulfophenyl or a group of the formula —SO$_2$—Y with Y of the above mentioned meanings, B[4] is hydrogen, alkyl of 1 to 4 carbons or alkyl of 1 to 4 carbons substituted by alkoxy of 1 to 4 carbons, sulfo, carboxy, sulfato, acetylamino, benzoylamino, cyano or a group of the formula —SO$_2$—Y with Y of the above mentioned meanings, or is alkenyl of 2 to 4 carbon atoms, cyclohexyl or phenyl which is optionally substituted by substituents selected from carboxy, sulfo, benzoylamino, acetylamino, a group of the formula —SO$_2$—Y with Y of the above mentioned meanings, and chlorine, k is zero or 1 (and in the case where k is zero, this group is hydrogen), m is 1 or 2, m$_1$ is 1, 2 or 3, W is sulfo, alkylsulfonyl of 1 to 4 carbons, phenylsulfonyl, bromine, fluorine or chlorine, D* is a group of the formula

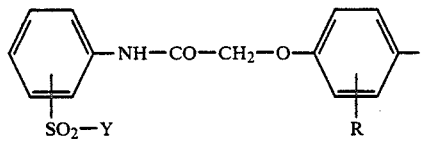

in which Y and R are defined as above, or

D* is phenyl which is optionally substituted by 1, 2 or 3 substituents selected from alkyl of 1 to 4 carbons, alkoxy of 1 to 4 carbons, chlorine, bromine, hydroxy, carboxy, sulfo, carbamoyl, sulfamoyl and alkanoylamino of 2 to 5 carbons, or substituted by a group of the formula —SO$_2$—Y with Y of the above mentioned meanings, or by a combination of those substituents, or is naphthyl substituted by 1, 2 or 3 sulfos, or by 1 or 2 sulfos and 1 or 2 groups of the formula —SO$_2$-Y with Y of the abovementioned meanings, or by one group —SO$_2$—Y;

K* is a group of the formula

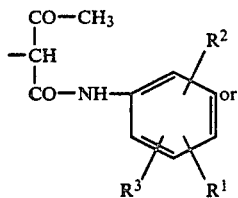

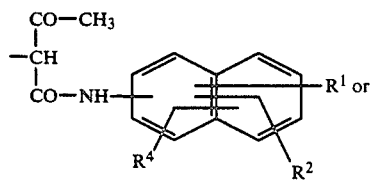

-continued

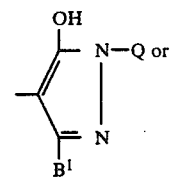

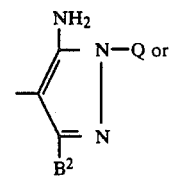

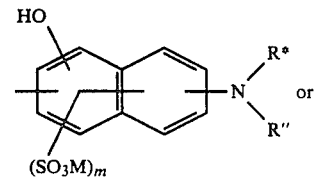

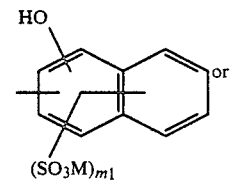

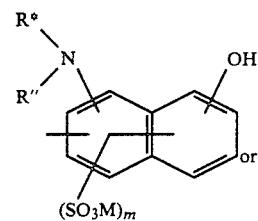

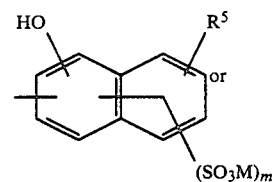

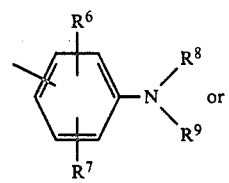

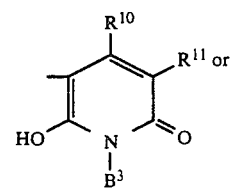

-continued

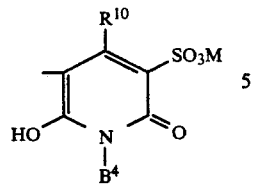

defined above.

2. A compound as claimed in claim 1, wherein K is a radical of the general formula

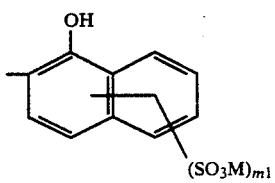

in which $m_1$ is the number 1, 2 or 3 and M is a hydrogen or an alkali metal.

3. A compound as claimed in claim 1, wherein K is a radical of the general formula

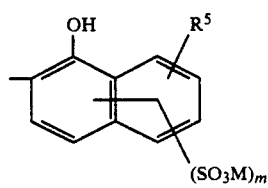

in which $R^5$ is benzoylamino or alkanoylamino of 2 to 5 carbons, m is the number 1 or 2 and M is hydrogen or an alkali metal.

4. A compound as claimed in claim 1, wherein K is a radical of the general formula

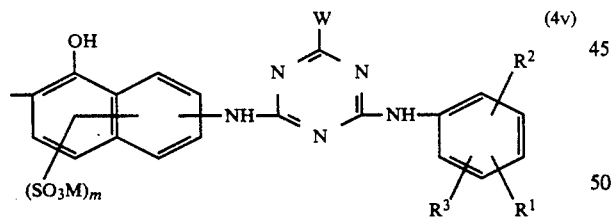

in which m is the number 1 or 2, W is sulfo, alkylsulfonyl of 1 to 4 carbons, phenylsulfonyl, bromine, fluorine or chlorine, $R^1$ is the group —$SO_2$—Y having one of the meanings mentioned in claim 1, $R^2$ is hydrogen, alkyl of 1 to 4 carbons, alkoxy of 1 to 4 carbons, chlorine, bromine, carboxy, sulfo or nitro, $R^3$ is hydrogen and M is hydrogen or an alkali metal.

5. A compound as claimed in claim 15, wherein K is a radical of the general formula

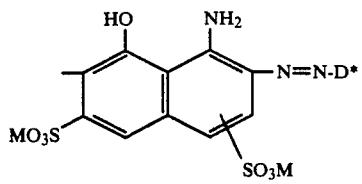

in which D* is phenyl, which is unsubstituted or substituted by 1, 2, or 3 substituents selected from the group consisting of alkyl of 1 to 4 carbons, alkoxy of 1 to 4 carbons, chlorine, bromine, hydroxy, carboxy, sulfo, carbamoyl, sulfamoyl and alkanoylamino of 2 to 5 carbons, or by a group of the general formula —$SO_2$—Y where Y has one of the meanings mentioned in claim 15, or a mixture thereof, or is naphthyl which is substituted by 1, 2, or 3 sulfo groups or by 1 or 2 sulfo groups and 1 or 2 groups of the general formula —$SO_2$—Y where Y has one of the meanings mentioned in claim 1 or only by one of these groups—$SO_2$—Y, and M is a hydrogen or an alkali metal.

6. A compound as claimed in claim 4, wherein W is fluorine or chlorine.

7. A compound as claimed in claim 5, wherein D* is phenyl which is substituted in the para position relative to the azo group by a group of the general formula —$SO_2$—Y where Y has the meaning mentioned in claim 1.

8. A compound as claimed in 1, wherein R is hydrogen.

9. A compound as claimed in claim 1, wherein Y is vinyl or β-sulfatoethyl.

10. A compound as claimed in claim 1 wherein Y is β-sulfatoethyl.

11. A compound of the general formula

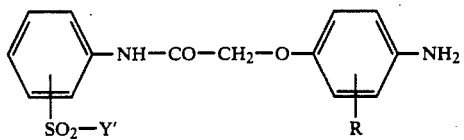

in which
G is amino or nitro,
R is hydrogen, nitro, alkyl of 1 to 4 carbons, alkoxy of 1 to 4 carbons, carboxy, hydroxy or halogen and
Y' is β-hydroxyethyl or vinyl or ethyl containing a substituent in the β-position which can be eliminated by alkali with the formation of a vinyl group.

12. A compound as claimed in claim 11, wherein Y' is β-hydroxyethyl, β-sulfatoethyl or vinyl.

13. A compound as claimed in claim 11, wherein R is hydrogen.

14. A compound as claimed in claim 12, wherein R is hydrogen.

* * * * *